United States Patent [19]

Bouwmeester

[11] 4,299,532

[45] Nov. 10, 1981

[54] MECHANISM FOR TRANSFERRING OBJECTS FROM ONE POSITION TO ANOTHER

[75] Inventor: Gerrit Bouwmeester, Almelo, Netherlands

[73] Assignee: U.S. Philips Corporation, New York, N.Y.

[21] Appl. No.: 111,138

[22] Filed: Jan. 10, 1980

[30] Foreign Application Priority Data

Jan. 12, 1979 [NL] Netherlands .................. 7900243

[51] Int. Cl.³ ........................................... B23Q 7/02
[52] U.S. Cl. ........................... 414/750; 414/753; 294/116; 198/486
[58] Field of Search .................. 414/222–225, 414/744 R, 744 A, 749–751, 753; 198/339, 480, 482, 803, 486; 74/57, 89; 294/115, 116

[56] References Cited

U.S. PATENT DOCUMENTS

| | | | |
|---|---|---|---|
| 3,233,751 | 2/1966 | Bannon | 414/753 X |
| 3,240,360 | 3/1966 | Richards | 414/744 A |
| 3,718,216 | 2/1973 | Wilson | 414/744 A X |
| 4,202,435 | 5/1980 | Mang et al. | 198/339 |

*Primary Examiner*—Trygve M. Blix
*Assistant Examiner*—Terrance L. Siemens
*Attorney, Agent, or Firm*—Thomas A. Briody; Robert T. Mayer; Paul R. Miller

[57] ABSTRACT

A mechanism for transferring objects from one position to another position in another turntable. A slide is mounted to be slidable on a guide on the turntable. The slide comprises a slot which extends transversely of the guide and in which a drive member is accommodated which is connected to one end of a first arm, the other end of which is pivotably connected to a second arm which is journalled in the turntable by way of a shaft and which is coupled to a drive. Around this shaft a wheel is rigidly arranged. This wheel is coupled to a further wheel, the center of which is formed by the pivot of the first and the second arm. This further wheel is rigidly connected to the first arm. The arrangement is such that, when the shaft is driven, the drive member follows an elliptical path. On the slide there is provided a gripping member for gripping and releasing the objects to be transferred.

2 Claims, 8 Drawing Figures

MECHANISM FOR TRANSFERRING OBJECTS FROM ONE POSITION TO ANOTHER

BACKGROUND OF THE INVENTION

The invention relates to a mechanism for transferring objects, notably samples, from one position to another.

Mechanisms of the kind forming the subject of the present invention are used, for example, in analysis apparatus for transferring the samples of given preparations from a position in which they are presented by a sample transport device to a position in which a measurement can be performed on these samples. After measurement, the samples must usually be returned to the transport device.

SUMMARY OF THE INVENTION

The present invention has for its object to provide a simple and compact mechanism for transferring samples from the one position to the other and vice versa.

The mechanism in accordance with the invention is characterized in that there is provided a turntable around which a plurality of positions may be present, a slide being slidably arranged on a guide on the turntable, the slide comprising a slot which extends transversely of the guide and in which a drive member (pin or roller) is accommodated which is secured to one end of a first arm, the other end of which is pivotably connected to a second arm which is journalled in the turntable by way of a shaft which is coupled to a drive, a wheel being rigidly arranged around this shaft, the wheel being coupled to a further wheel whose center is formed by the pivot of the first and the second arm and which is rigidly connected to the first arm, the arrangement being such that, when the shaft is driven, the drive member follows an elliptical path, the slide accommodating a gripping member for gripping and releasing the objects to be transferred.

The mechanism in accordance with the invention has a compact and simple construction. By rotation of the turntable, for example, by means of a maltese cross drive through, for example, 180°, the slide is moved from the one position opposite the other position. The slide is subsequently moved outwards into the relevant position, by means of the drive member, after which a sample is gripped or released, depending on the situation. The exact operation will be described in detail with reference to the Figures.

In a further embodiment of the mechanism in accordance with the invention, a structural member which is movable against spring force is mounted on the slide, part of said member extending in said slot and being operable by the drive member, the structural member furthermore bearing against the gripping member and determining the position thereof.

BRIEF DESCRIPTION OF THE DRAWING

The invention will be described in detail hereinafter with reference to the drawing.

DESCRIPTION OF THE INVENTION

Figure 4:
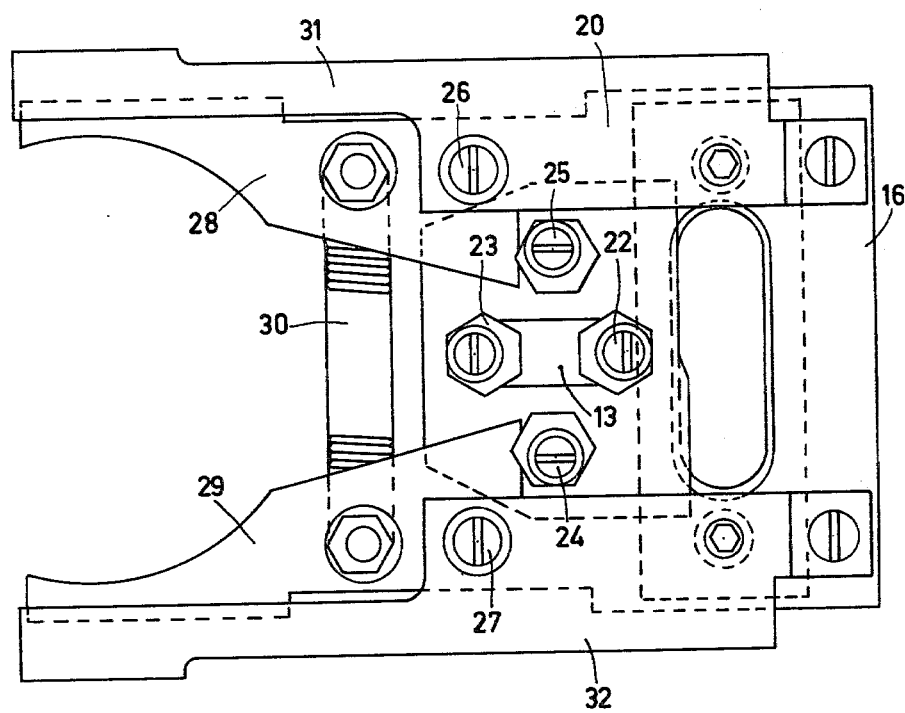
FIGS. 4 and 5 are a plan view and a sectional view, respectively, of the slide.
Figure 5:
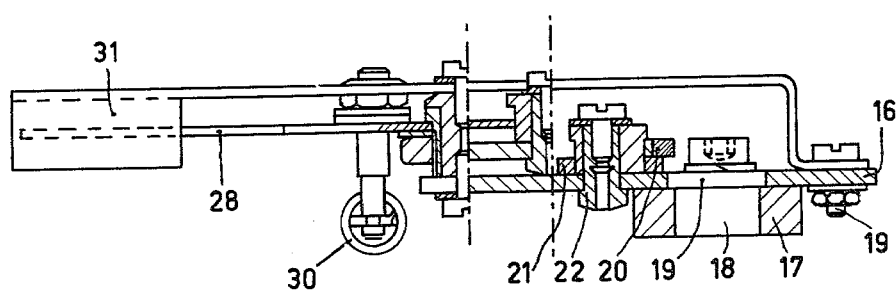

A hub-like structural member 3 supports a structural member 12 which supports two beams 14 and 15. The beams 14 and 15 serve as rails for a slide construction which is shown in detail in the FIGS. 4 and 5. This slide comprises a plate-shaped basic section 16 which is guided in grooves in the beams 14 and 15. The lower side of this basic section comprises a structural member 17 which is provided with a groove 18 which is slightly smaller than a corresponding recess 19 in the basic section 16. At some distance above the basic section there is arranged a plate 20 which is slidable on spacer plates 21 which are arranged around bolts 22 and 23. The bolts 22, 23 are provided in the basic section and pass through a slot-like recess 13 in the plate 20, so that the movement of this plate is guided by the bolts 22, 23.

The plate 20 supports two abutments 24, 25 which bear against two arms 28, 29 which are pivotable around points 26, 27. The arms 28, 29 are interconnected by a tension spring 30 which draws the arms towards each other and against the abutments 26, 27. Two side pieces 31 and 32 which extend on either side of the slide serve, in conjunction with the plate 16, for guiding the slide in the beams 14, 15. In a bore 33 in the hub-like structural member 3 a shaft 34 is journalled by way of bearings 35, 36. A second arm 37 is rigidly connected to the shaft 34. In the end of the arm 37 which is remote from the shaft 34 a shaft 38 is rotatably journalled. A first arm 39 is rigidly connected to this shaft, with the arm comprising a pin 39' which extends through the slot-like recess 18, 19 of the slide and which comprises a roller 41 which cooperates with the plate 20 and a roller 42 which cooperates with the walls of the slot 18 in the structural member 17.

The shaft 38 furthermore comprises a toothed wheel 43 on which a toothed belt 44 is guided which connects the wheel 43 to a further toothed wheel 45 which is rigidly connected to the hub-like member.

A flange 46 is rigidly connected to the other side of the hub-like member 3. A second flange 48 is connected to the flange 46 by means of a number of bolts with spacer bushers 47, said second flange supporting an electric motor and transmission combination 49. The driving shaft 50 of this combination is coupled to the shaft 34.

A roller 52 on an arm 53 which is capable of rotation around a point 54 and which is pulled towards the plate 1 by a spring 55 engages the slots 2 and ensures that the plate 1 is more or less locked when it is not moved by the rollers 10 and 11, so that it cannot perform an undesirable movement.

Figure 1:
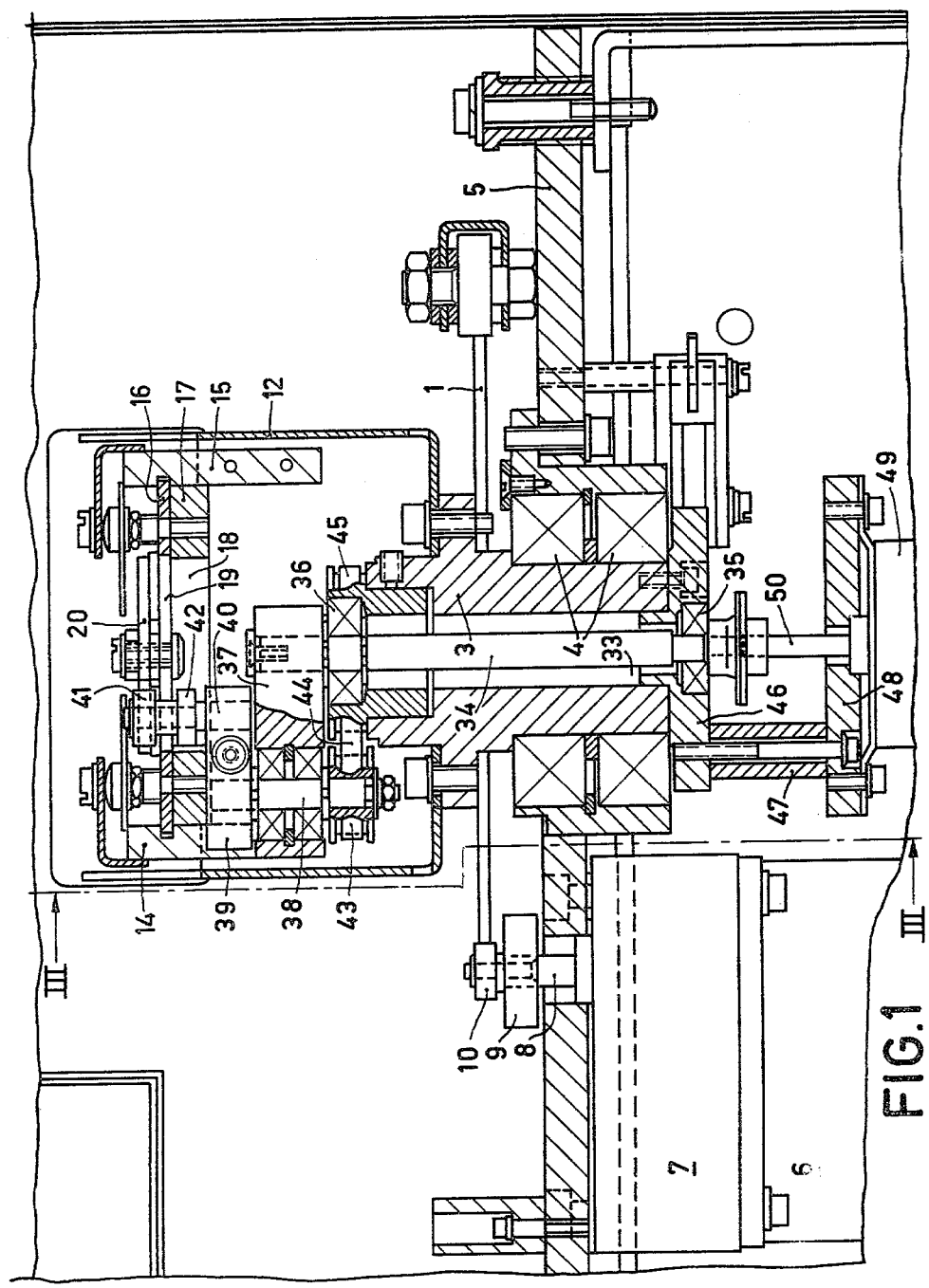
FIGS. 1, 2 and 3 show a mechanism for transferring objects: a sectional view taken along the line I—I of FIG. 2, a plan view with the slide removed, and a sectional view taken along the line III—III of FIG. 1, respectively.
Figure 2:
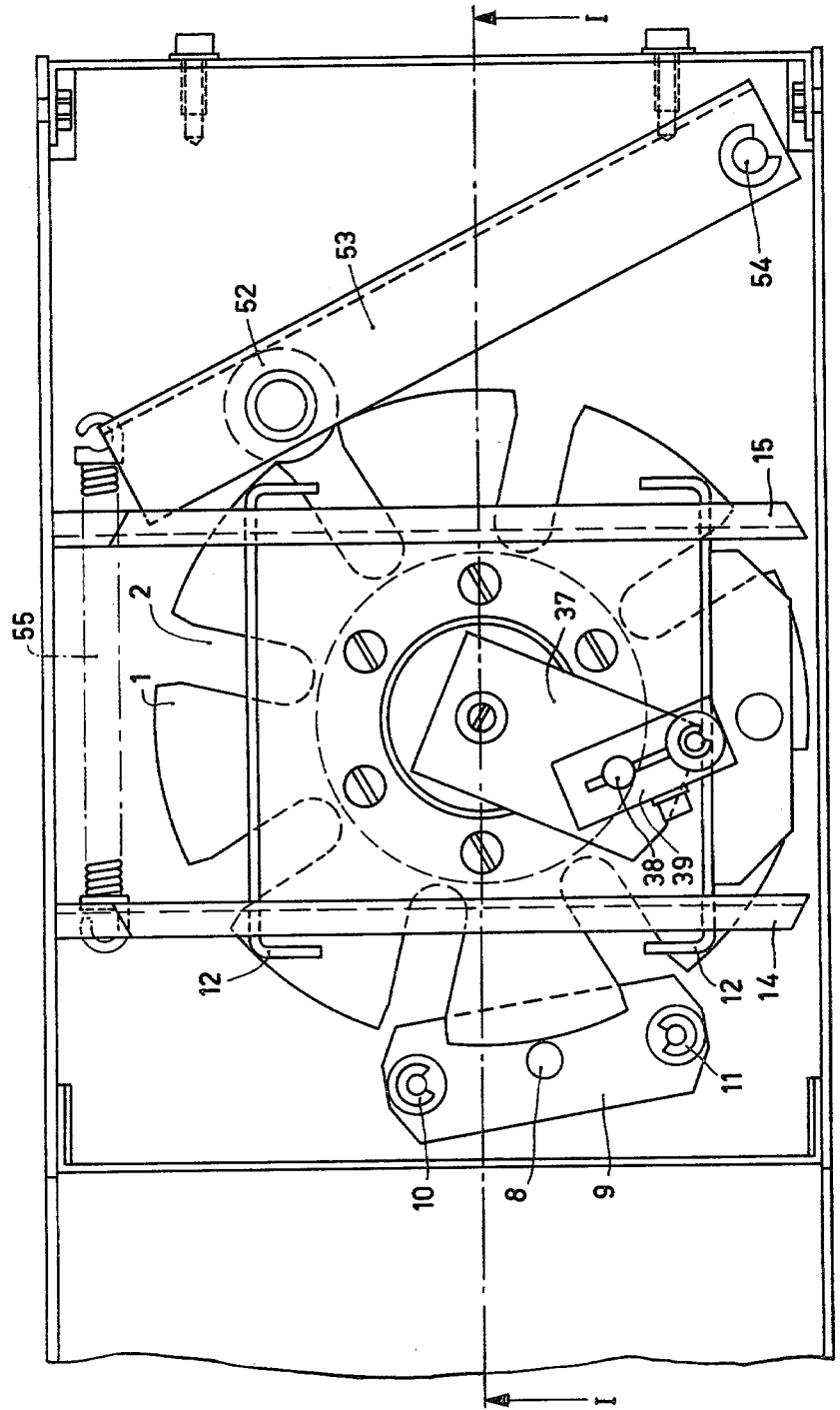
Figure 3:
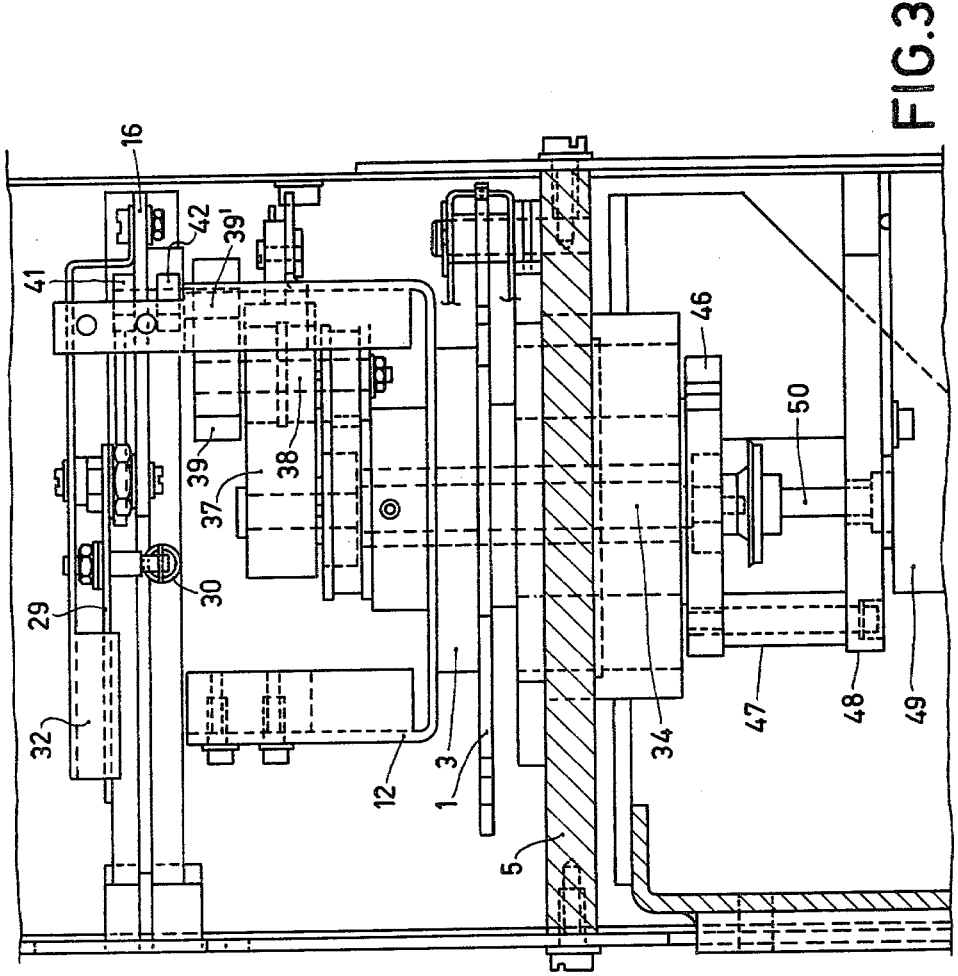
Figure 7:
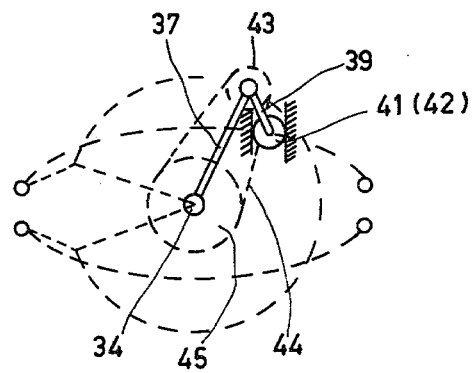
Figure 8:
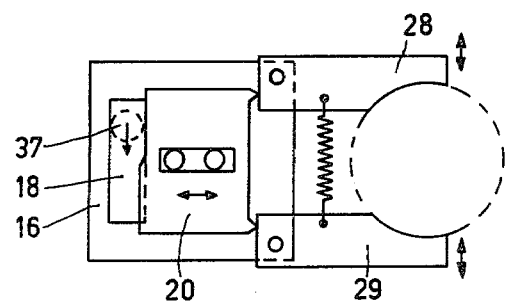

The operation of the device will be described in detail with reference to the FIGS. 6, 7, 8 which diagrammatically show the device according to the FIGS. 1, 2 and 3.

Figure 6:
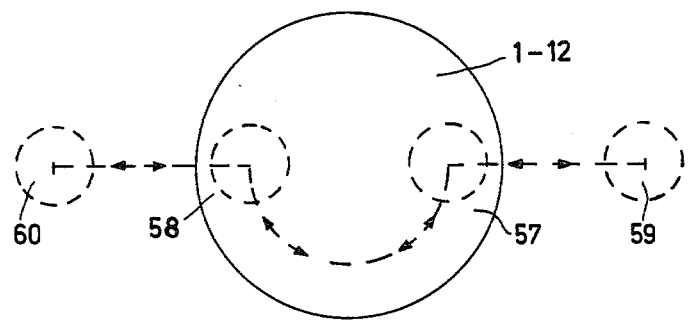
FIGS. 6, 7 and 8 diagrammatically illustrate the operation of the mechanism.

FIG. 6 shows how the turntable 1-2 accommodating the slide 16 can be rotated between two positions 57 and 58. In the position 57, the slide is situated opposite a measuring position 59 in which a sample transported by the slide can be measured; in the position 58, the slide is situated opposite a storage position 60 wherefrom the slide can take a sample and return it at a later stage.

The rotation of the turntable construction is realized by means of an electric motor 6 whch rotates the arm 9 and the rollers 10 and 11 accommodated thereon, thus causing rotation of the plate 1 until it has been rotated through 180°. The slide and everything connected thereto is then displaced, for example, from the storage position 58 to the measuring position 57.

During this rotation, the position of the slide with respect to the turntable does not change, because the hub 3 and everything connected thereto also rotates. In the position 57, this slide must be moved to the measuring position where the sample must be put down, and be returned again.

This is realized as follows. The shaft 34 is rotated by means of an electric motor 49. As a result, the arm 37 is moved and also the arm 39. Due to the coupling of these arms by means of the wheels 53, 45 and the toothed belt 44, the rollers 41, 42 connected to the end of the arm 39 start to describe an elliptical path. When the roller 42 moves to the right over the upper part of the elliptical path, the roller 42 is present in the upper half of the slot 18 (see FIG. 8) and the slide is moved to the right until it arrives in the measuring position. The roller 41 then arrives in the lower part of the slot 19 (see FIG. 8); the plate 20 is then pressed to the right over a small distance (by the roller 41). As a result, the jaws 28, 29 are opened. The sample is then released and, when the roller 42 moves further over the lower part of the elliptical path, the slide with the open jaws is moved to the left until it is completely out of the range of the measuring station again. After the measuring process, the roller 41 is moved over the elliptical path in the reverse direction. This means that the slide moves to the measuring position with opened jaws. In the measuring position, due to the fact that the roller 41 releases the plate again, the jaws are closed again, under the influence of the spring 30, and clamp the sample. The slide is subsequently moved out of the range of the measuring station with its jaws closed and the sample clamped there between.

Subsequently, the turntable is rotated through 180°, so that the slide arrives in front of the storage position, after which the roller 42 is moved over its elliptical path again in the described manner.

The foregoing description concerns the situation where samples must be transported between diametrically oppositely situated position. In given circumstances it is also possible to arrange a plurality of positions around the turntable and to transport samples to and from between these positions.

What is claimed is:

1. A mechanism for transferring objects, notably samples, from one position to another, characterized in that the mechanism comprises a turntable around which a plurality of positions may be present, a slide being slidably arranged on a guide on the turntable, said slide comprising a slot which extends transversely of the guide and in which a drive member (pin or roller) is accommodated which is secured to one end of a first arm, the other end of which is pivotably connected to a second arm which is journalled in the turntable by way of a shaft and which is coupled to a drive, a wheel being rigidly arranged around this shaft, said wheel being coupled to a further wheel whose centre is formed by the pivot of the first and the second arm and which is rigidly connected to the first arm, the arrangement being such that, when the shaft is driven, the drive member follows an elliptical path, the slide accommodating a gripping member for gripping and releasing the objects to be transferred.

2. A mechanism as claimed in claim 1, characterized in that the slide accommodates a structural member which is slidable against spring force, part of said structural member extending in said slot and being operable by the drive member, the structural member furthermore bearing against the gripping member and determining the positioning thereof.

* * * * *